United States Patent [19]

Forssen

[11] Patent Number: 4,769,250
[45] Date of Patent: Sep. 6, 1988

[54] ANTRACYCLINE ANTINEOPLASTIC AGENTS ENCAPSULATED IN PHOSPHOLIPID VESICLE PARTICLES AND METHODS FOR USING SAME FOR TUMOR THERAPY

[75] Inventor: Eric A. Forssen, La Canada, Calif.

[73] Assignee: Vestar, Inc., San Dimas, Calif.

[21] Appl. No.: 112,073

[22] Filed: Oct. 26, 1987

Related U.S. Application Data

[63] Continuation-in-part of Ser. No. 787,535, Oct. 15, 1985, abandoned.

[51] Int. Cl.$^4$ ............................................. A61K 9/50
[52] U.S. Cl. .................................. 424/450; 424/491; 424/493; 514/908
[58] Field of Search ...................... 424/450, 491, 493; 514/908; 252/316

[56] References Cited

U.S. PATENT DOCUMENTS

| | | | |
|---|---|---|---|
| 4,310,505 | 1/1982 | Baldeschwieler et al. | 252/316 |
| 4,331,654 | 5/1982 | Morris | 424/450 |
| 4,356,167 | 10/1982 | Kelly | 424/450 |
| 4,411,894 | 10/1983 | Schrank et al. | 424/244 |
| 4,427,649 | 1/1984 | Dingle et al. | 424/450 |
| 4,427,664 | 1/1984 | Horton et al. | 514/908 |
| 4,438,105 | 3/1984 | Suarato et al. | 514/908 |
| 4,474,945 | 10/1984 | Yoshimoto et al. | 514/908 |
| 4,619,794 | 10/1986 | Hauser | 424/450 |

FOREIGN PATENT DOCUMENTS

WO85/00968 3/1985 PCT Int'l Appl. .
2002319A 2/1979 United Kingdom .
2146525A 4/1985 United Kingdom .

OTHER PUBLICATIONS

Mosijezuk, et al., Cancer, 44, pp. 1582-1587, (1979).
Lefrak, et al., Cancer, 32, pp. 302-314, (1973).
Forssen and Tokes, Cancer Res., 43, pp. 546-550, (1983).
Gabizon et al., Cancer Res., 43, pp. 4730-4735, (1983).
Gregoriadis, "Liposome Technology", vol. 1, Preparation of Liposomes, (Boca Raton, Fla.: CRC Press Inc., 1984); Strauss, Freezing and Thawing of Liposome Suspensions", pp. 197-219.
Gabizon et al., Br. J. Cancer, 51, pp. 681-689, (1985).
M. R. Mauk and R. C. Gamble, Anal. Bioc., 94, pp. 302-307, (1979).
Gabizon et al., Cancer Res., 42, 4734-4739, (1982).

Primary Examiner—Ronald W. Griffin
Attorney, Agent, or Firm—Lyon & Lyon

[57] ABSTRACT

Formulations consisting of phospholipid bilayer membrane particles made from mixtures of anionic and neutral phospholipids encapsulating anthracycline anti-neoplastic agents, suspended in a low ionic strength aqueous phase, are described. In a preferred embodiment, the particles are in the form of vesicles which comprise daunorubicin, distearoyl phosphatidylglycerol and distearoyl phosphatidylcholine, the mol ratio of daunorubicin to distearoyl phosphatidylglycerol is at least about 1:1.25, and the suspending medium is an aqueous lactose solution containing a small amount of base.

18 Claims, 12 Drawing Sheets

DAUNOMYCIN BIODISTRIBUTION: Free and Vesicle Entrapped Blood Levels of C-14 Daunomycin *

Hours Following i.v. Administration
Daunomycin Dosed at 5mg/Kg

* In Figures 1 through 8 the anthracycline agent daunorubicin is labeled "daunomycin".

FIG. 12

ANTRACYCLINE ANTINEOPLASTIC AGENTS ENCAPSULATED IN PHOSPHOLIPID VESICLE PARTICLES AND METHODS FOR USING SAME FOR TUMOR THERAPY

This application is a continuation-in-part of copending U.S. patent application Ser. No. 787,535, filed Oct. 15, 1985, now abandoned, in the name of Eric A. Forssen and of common assignment with this application.

FIELD OF INVENTION

This invention relates to compositions consisting of phospholipid encapsulated anthracycline anti-neoplastic agents. In another aspect it relates to the use of such compositions to deliver chemotherapeutic agents to tumors in a body.

BACKGROUND

Daunorubicin (also known as daunomycin), doxorubicin (also known as Adriamycin), Aclacinomycin A and other cationic anthracycline anti-neoplastic agents are currently of great clinical interest for the treatment of tumors, including most leukemias and solid tumors. Structurally, these compounds consist of a hydrophobic tetracycline ring system coupled to an amino sugar through a glycoside linkage. These anthracycline agents associate with phosphate containing materials, and exhibit a high affinity with, for example, cardiolipin. These compounds have been shown to exhibit marked activity against a wide variety of neoplasms. However, the clinical use of these drugs in humans has been limited by the chronic toxic effect of the drugs on heart tissue. Children for example, are highly susceptible to doxorubicin-induced congestive heart failure. Mosijezuk, et al., Cancer, 44, p. 1582–1587 (1979). Long-term administration of such drugs leads to an increased risk of cardiomyopathy. Lefrak et al., Cancer, 32, p. 302–314 (1973).

Phospholipid bilayer membrane particles in the form of unilamellar vesicles known as liposomes have received increasing attention as possible carriers for anthracycline drugs. Certain formulations have been shown to increase antitumor activity, alter in vivo tissue distribution and decreas toxicity.

Difficulties have been encountered in producing encapsulated anthracyclines. In part this has been due to the surfactant or detergent-like effect these compounds exert on the phospholipid vesicle bilayer, causing leakage and creating vesicle instability. Another problem has been the aggregation of such vesicles during storage. In addition, the efficiency of entrapment of previous formulations of encapsulated anthracyclines has been low, and has been reported to be between 5 and 65%. Forssen and Tokes, Cancer Res. 43, p. 546–550 (1983); and Gabizon et al., Cancer Res. 43, p. 4730–4735 (1983); and Gabizon et al., Br. J. Cancer 51, p. 681–689 (1985). Thus it has not been possible to achieve large scale production of stable, encapsulated anthracyclines for therapeutic purposes.

Accordingly, it is an object of the present invention to provide improved formulations for encapsulating anthracycline anti-neoplastic agents in phospholipid bilayer membrane particles.

Another object of this invention is to provide a method fo using improved formulations of encapsulated anti-neoplastic agents to provide decreased cardiotoxicity and increased antitumor efficacy in humans.

The manner in which these and other objects are realized by the present invention will be apparent from the summary and detailed description set forth below.

SUMMARY OF THE INVENTION

Compositions comprising anthracycline anti-neoplastic agents encapsulated in phospholipid bilayer membrane particles consisting, in one embodiment, of anionic phospholipids such as distearoyl phosphatidylglycerol admixed with neutral phospholipids such as distearoyl phosphatidylcholine are described. In another embodiment of this invention the composition can also contain cholesterol or like-acting substances, but this is not essential to the practice of the invention. The particles are suspended in a low ionic strength aqueous phase such as an aqueous solution of a physiologically acceptable nonionic hydroxyl-containing compound, e.g., a monosaccharide such as dextrose or a polysaccharide such as lactose. This low ionic strength aqueous phase will be one having as low a content of extraneous anions, e.g., chloride ions from an anthracycline antineoplastic agent such as daunorubicin hydrochloride, as can practicably be achieved, e.g., an anion concentration of about 5 mMolar (millimolar) or less, and a pH preferably between about 6.0 and about 8.0.

A particularly preferred composition comprises daunorubicin, distearoyl phosphatidylglycerol and distearyol phosphatidylcholine in a molar ratio of these components of 1:1.5:7, respectively, suspended in an aqueous phase comprising a disaccharide such as lactose, preferably a 9–11% lactose solution containing 5 mM TRIS base (Tromethamine or 2-amino-2-hydroxymethyl-1,3-propanediol) at a pH of about 6.0 to 8.0.

These compositions may be administered in multiple doses to a human subject to treat tumors.

BRIEF DESCRIPTION OF THE DRAWINGS

The vesicles for which the results illustrated in FIGS. 1–8, inclusive were obtained were those of Example I hereinbelow.

FIG. 9 illustrates the uptake of tritiated daunorubicin by whole blood, tumor tissue (P-1798 lymphosarcoma)

and three other tissues in mice as determined for the daunorubicin-containing vesicles of Examples II, III and IV hereinbelow, for free daunorubicin and for daunorubicin simply admixed with distearoyl phosphatidylglycerol in a 1:1 mol ratio.

DETAILED DESCRIPTION OF THE INVENTION

As indicated above, according to this invention encapsulation and improved delivery of anthracycline anti-neoplastic agents useful in treating tumors in humans is achieved using compositions containing bilayer membrane particles, preferably in the form of small, unilamellar vesicles consisting of a mixture of anionic and neutral phospholipids, and a cationic anthracycline anti-neoplastic agent, suspended in a low-ionic strength aqueous phase in which a physiologically acceptable nonionic hydroxyl-containing compound is dissolved and which contains as low a content of extraneous anions as can practicably be achieved.

That anthracyclines exhibit a high affinity for the phospholipid cardiolipin appears to be of particular importance for mediating the biological activities of these drugs. Cardiolipin, however, is not a desirable constituent for phospholipid vesicles in spite of its high affinity for anthracyclines because when interacting with an anthracycline such as daunorubicin it forms micelles which destabilize the bilayer structure of encapsulating particles such as liposomes. Cardiolipin is also known to be highly antigenic in nature when incorporated in liposome membranes, and thus may cause an increased immunogenic response when injected into a body.

As noted above, one of the difficulties associated with the entrapment of anthracycline anti-neoplastic agents in phospholipid bilayer membrane particles is their amphiphilic nature, which can cause these drug molecules to attempt to partition nearly equally between aqueous and lipid media. This partitioning can, in turn, cause these drugs to easily leak from lipid membranes and can disrupt the membranes themselves, destroying the vesicles' bilayer structure. An advantage of using an anionic phospholipid such as distearoyl phosphatidylglycerol is that it has a negative charge which can be used to cancel the positive charge on the cationic anthracycline molecule. This permits the production of neutral vesicles which resist disruption and leakage. Furthermore, the use of a low-ionic strength aqueous phase to suspend the vesicles improves vesicle stability because it inhibits vesicle aggregation.

An additional advantage of using such negatively charged phospholipids is that the cancellation of the charge on the anthracycline molecule permits the formation of a water insoluble salt between the phospholipid and the anthracycline. This complex increases the affinity of the drug for the hydrophobic bilayer of the vesicle, and although I do not wish to be bound by any particular theory or mechanism advanced to explain the operation of this invention, I believe that the drug becomes entrapped in the vesicle membrane itself rather than simply being present within the vesicle's interior aqueous space. While an anthracycline such as daunorubicin will bind fairly strongly to a negative phospholipid such as distearoyl phosphatidylglycerol with a binding constant of approximately $10^5 M^{-1}$, its affinity for binding to DNA in a cell is much greater, on the order of $2 \times 10^6 M^{-1}$. Thus, the drug will be able to be released from the distearoyl phosphatidylglycerol and to complex with DNA present in the target tumor cells.

The micellular particles of this invention are preferably in the form of small [less than about 60 nm (nanometers), and preferably about 45–55 nm in diameter] unilamellar phospholipid vesicles prepared by sonication as described by M. R. Mauk and R. C. Gamble, *Anal. Bioc.*, 94, p. 302–307 (1979), or by microemulsification using the procedures described in Gamble copending U.S. patent application filed Jan. 31, 1985, Ser. No. 696,727, of common assignment with this application. Vesicles prepared in this fashion having the types and amounts of components taught by this invention exhibit a high efficiency of entrapment (greater than 90%) of the anthracycline anti-neoplastic agent, a good storage life (about 90% particles intact after two weeks), adequate targeting of the drug to tumor tissue and little or no tendency to aggregate. One advantage of the higher entrapment efficiency is that the step of separating free drug from entrapped drug after loading procedures may be eliminated, thus simplifying manufacture.

Adjustment of pH is an additional factor for maximum drug entrapment when practicing this invention, with the optimal pH range being from about 6.0 to 8.0. A suitable substance for adjusting pH is TRIS base (Tromethamine or 2-amino-2-hydroxymethyl-1,3-propanediol) since it can readily be buffered over a pH range of 7 to 9. Other bases such as sodium hydroxide or potassium hydroxide, amine bases such as N-methylglucamine, and the like, which will not contribute unwanted anions, can also be used.

It has been found in the present invention that by using anionic phospholipids such as distearoyl phosphatidylglycerol (sometimes referred to hereinafter as DSPG) with neutral phospholipids such as distearoyl phosphatidylcholine (sometimes referred to hereinafter as DSPC), the partitioning of an anthracycline anti-neoplastic agent such as daunorubicin (sometimes referred to hereinafter as DAU) into the lipid phase may be increased, leading to increased entrapment of the anthracycline anti-neoplastic agent in the micellular particle and more stable particles. The incorporation of cholesterol (sometimes referred to hereinafter as CHOL) ca further improve the stability of the particles encapsulating the anthracycline anti-neoplastic agent, and in all cases the stability of these compositions is further enhanced by suspending the particles in a low-ionic strength aqueous phase in which a physiologically acceptable anionic hydroxyl-containing compound is dissolved and which contains as low a content of extraneous anions as can practicably be achieved.

Among the anionic phospholipids which can be employed in practicing this invention are phosphatidylglycerols, phosphatidylserines, phosphatidylinositols and phosphatidic acids, such as distearoyl phosphatidylglycerol, dipalmitoyl phosphatidylglycerol, distearoyl phosphatidylserine, dioleoyl phosphatidylinositol, and the like. Neutral phospholipids which can be used together with an anionic phospholipid include phosphatidylcholines and phosphatidylethanolamines, such as distearoyl phosphatidylcholine, 1-palmitoyl-2-oleoyl phosphatidylcholine, dilinoleoyl phosphatidylethanolamine, and the like.

The mol ratio of anthracycline anti-neoplastic agent to total phospholipid [anionic plus neutral phospholipid(s)] in the compositions of this invention should preferably be no more than about 1:20, with mol ratios of about 1:10 or less being particularly preferred, although there is no upper limit, other than one imposed by the practical considerations one faces when working with injectable substances, on the total amount of phospholipids which can be used. The mol ratio of anthracycline anti-neoplastic agent to the anionic phospholipid(s) alone will be at least about 1:1.25, and preferably at least about 1:1.5. From about 1 to about 50 percent, and preferably from about 10 to about 20 percent, by weight, of the total weight of phospholipids present will preferably be anionic phospholipid(s), the balance being neutral phospholipid(s), but here too these amounts are not critical.

Compositions prepared in accordance with this invention having the aforementioned drug to anionic phospholipid mol ratios, particularly when prepared using an aqueous 9-11% lactose solution containing a small amount of base - typically 5 mM TRIS base - have been found to provide adequate targeting of the drug to tumor tissue (targeting efficiencies of about 90% or more have been observed) while, at the same time, limiting or eliminating the tendency of the phospholipid vesicles to aggregate. And, since neutral vesicles appear to be more effective for delivering anthracycline anti-neoplastic agents to tumors (see Mauk and Gamble, loc. cit.), the foregoing ratios of anthracycline anti-neoplastic agent to phospholipid components, which minimize the net negative charge of the vesicles while maintaining the physical integrity of the vesicles' structure by preserving the stability of the drug in the bilayer, are generally preferred when practicing this invention for this reason as well.

Cholesterol and like-acting substances, e.g., other sterols, when used, can be present in the compositions of this invention in mol ratios of cholesterol or the like to total phospholipid(s) ranging from about 1:1 to about 0:1, respectively, and in mol ratios of cholesterol or the like to anthracycline anti-neoplastic agent ranging from about 0:1 to about 20:1, respectively.

To prepare vesicles, the lipids and anthracycline anti-neoplastic agent, daunorubicin for example, to be used for vesicle preparation are weighed out in the desired ratios and are either dissolved in an organic solvent such as methanol or chloroform or kept until use as dry powders. If a solvent is used, it must be removed prior to the addition of the aqueous phase, by evaporation, for example under argon or nitrogen, or by application of a vacuum.

The aqueous phases preferred for formulation of anthracycline vesicles with high entrapment and maximum stability are low-ionic strength media which contain one or more physiologically acceptable nonionic hydroxyl-containing compounds and which also contain a low or minimal amount of extraneous anions. Extraneous anions include, for example, chloride ions from an anthracycline anti-neoplastic agent such as daunorubicin hydrochloride, and will be present in amounts as low as can practicably be achieved, e.g., an anion concentration of about 5 mM or less, such as can be achieved in sugar solutions in deionized distilled water. Sugars which can be used include monosaccharides such as dextrose, fructose and galactose and disaccharides such as lactose, sucrose, maltose and trehalose. An aqueous 9-11% lactose solution containing a small amount of base, e.g., 5 mM TRIS base, is particularly preferred. Such solutions minimize drug leakage from vesicles and decrease vesicle aggregation, and are well suited for parenteral use, for example human intravenous injection.

In order that those skilled in the art can more fully understand this invention, the following examples, which describe the preparation, characterization and in vivo chemotherapeutic application in animal models of vesicle formulations of this invention, are set forth. These examples are presented solely for purposes of illustration and are not intended to limit the present invention in any way.

EXAMPLE I

Daunorubicin Vesicles

A. Preparation of Vesicles Encaosulatinc Daunorubicin

Phospholipid vesicles were prepared using distearoyl phosphatidylglycerol, distearoyl phosphatidylcholine, cholesterol and daunorubicin in a molar ratio of DAU:DSPG:DSPC:CHOL of 1:4:5:6.

The lipids were obtained from Avanti Polar Lipids, (Birmingham, Alabama) and the daunorubicin was obtained from Sigma Chemical Co., (St. Louis, Missouri). These compounds were weighed out in the desired ratios and were dissolved in the organic solvent chloroform. The solvent was removed prior to addition of the aqueous phase by evaporation under nitrogen gas followed by vacuum. The non-ionic aqueous phase, consisting of 5% dextrose solution in water, pH adjusted to 7.4 with sodium hydroxide, was added to the lipid mixture and the solution was heated in a water bath at 60° to 70° C. for 1 to 3 minutes then vigorously agitated to form a suspension of the drug-lipid mix. This step was repeated until all the material had been suspended in the aqueous phase. This mixture was then sonicated using a needle probe sonicator (Sonics and Materials, Danbury, Conn.), at an output control setting of 1-2 (on a scale of 10). The sample was sonicated until clear, about 2-5 minutes for a 5 ml sample. During sonication the mixture was heated at 10° to 80° C. in a water bath. Following sonication, the sample was centrifuged to remove all particulate matter.

B. Characterization of Vesicles Encapsulating Daunorubicin

The vesicles containing daunorubicin, prepared as described above, were characterized for size (diameter) and entrapment efficiency following preparation. Vesicle sizing was performed using a Laser Particle Sizer Model 200 (Nicomp Instruments, Santa Barbara, Calif.) and was determined to be in the range of 45 to 55 nanometers in diameter.

The efficiency of association of daunorubicin within the vesicles was estimated using Sephadex G 50 gel-filtration to separate free from entrapped daunorubicin. Using the above formulations, 90-100% of the daunorubicin was found to be associated with the vesicles. Due to this high association, additional separation steps were unnecessary to remove free drug.

The daunorubicin vesicles prepared as described above were examined using HPLC and were found to be stable as indicated by the lack of chemical decomposition comparing freshly sonicated vesicles with those left at room temperature for two weeks. In addition, when a 2 ml sample of these vesicles were frozen in dry ice and later thawed at 65° C., the vesicles maintained their original size a determined by light scattering using the Laser Particle Sizer, and also retained all of the previously entrapped daunorubicin as determined by Sephadex gel filtration. Finally, incubation of Indium-III loaded daunorubicin vesicles in serum at 37° C. for 24 hours following the procedures described by Mauk and Gamble, loc. cit., for loading In-III in phospholipid vesicles, demonstrated no loss in entrapped In-III had occurred as determined by x-ray perturbed angular correlation ("PAC") (no decline in $G_{22}$).

C. Biodistribution of C-14 Labeled Daunorubicin Vesicles

Biodistribution studies of C-14 labeled daunorubicin, both free and vesicle entrapped, were conducted using a daunorubicin dose of 5 mg/kg in $CD_2F_1$ mice bearing intradermal P-1798 lymphosarcoma solid tumor. Time points were taken at 1, 4, 24 and 48 hours. The results are presented in FIGS. 1 through 4 showing that daunorubicin vesicles remain in the blood for longer periods of time than free drug and that in tumor tissue the level of vesicle encapsulated daunorubicin was significantly higher than free daunorubicin.

D. Toxicity

It appears that daunorubicin vesicles are not more toxic and are most likely less toxic than unencapsulated drug in animals bearing tumors as determined by survival in a small sample of mice using doses of 10, 20 and 30 mg/kg. In this limited study, toxicity induced deaths occurred only for the high dose unencapsulated daunorubicin (30 mg/kg), at a 100% rate. In contrast, no deaths occurred in mice receiving an equal dose of vesicle encapsulated daunorubicin.

E. Chemotherapeutic Efficacy of Daunorubicin Vesicles $CD_2F_1$ mice implanted with intradermal P-1798 solid lymphosarcoma received free and vesicle-encapsulated daunorubicin in a single dose injection of 20 mg/kg, and in multiple dosages of 5, 10 and 20 mg/kg.

In the first investigation, groups of 10 mice received free daunorubicin or daunorubicin-vesicles in 20 mg/kg single doses at three or four days following tumor implantation. Tumors were measured using calipers and the survival over time of treated and control mice was recorded. Controls consisted of injections of a 5% dextrose in water solution at 2 ml/20 gm doses.

Figure 1:
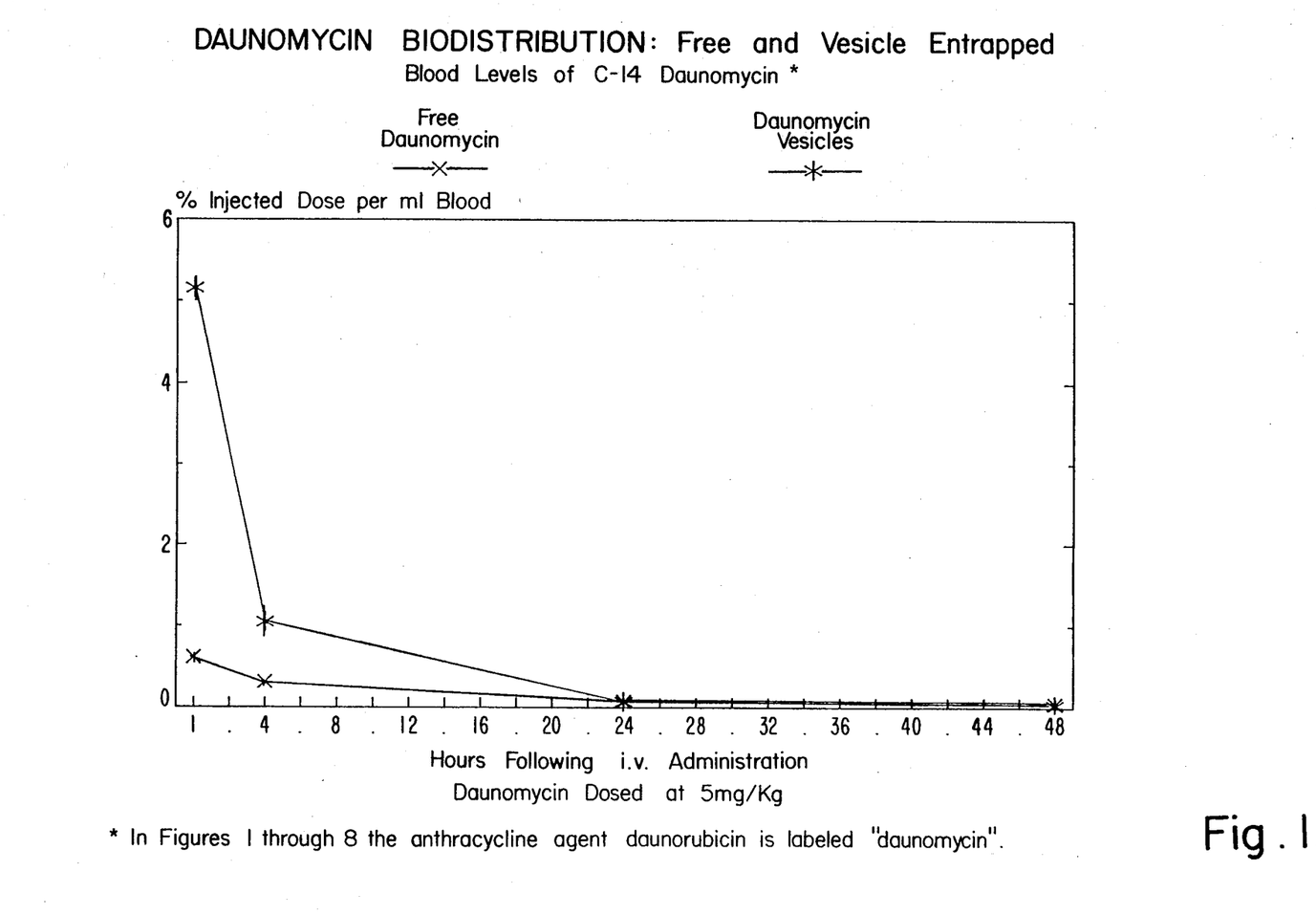
FIG. 1 illustrates the in vivo levels (biodistribution) of C-14 labeled daunorubicin, free and vesicle entrapped in the blood in mice at 1, 4, 24 and 48 hours.
Figure 2:
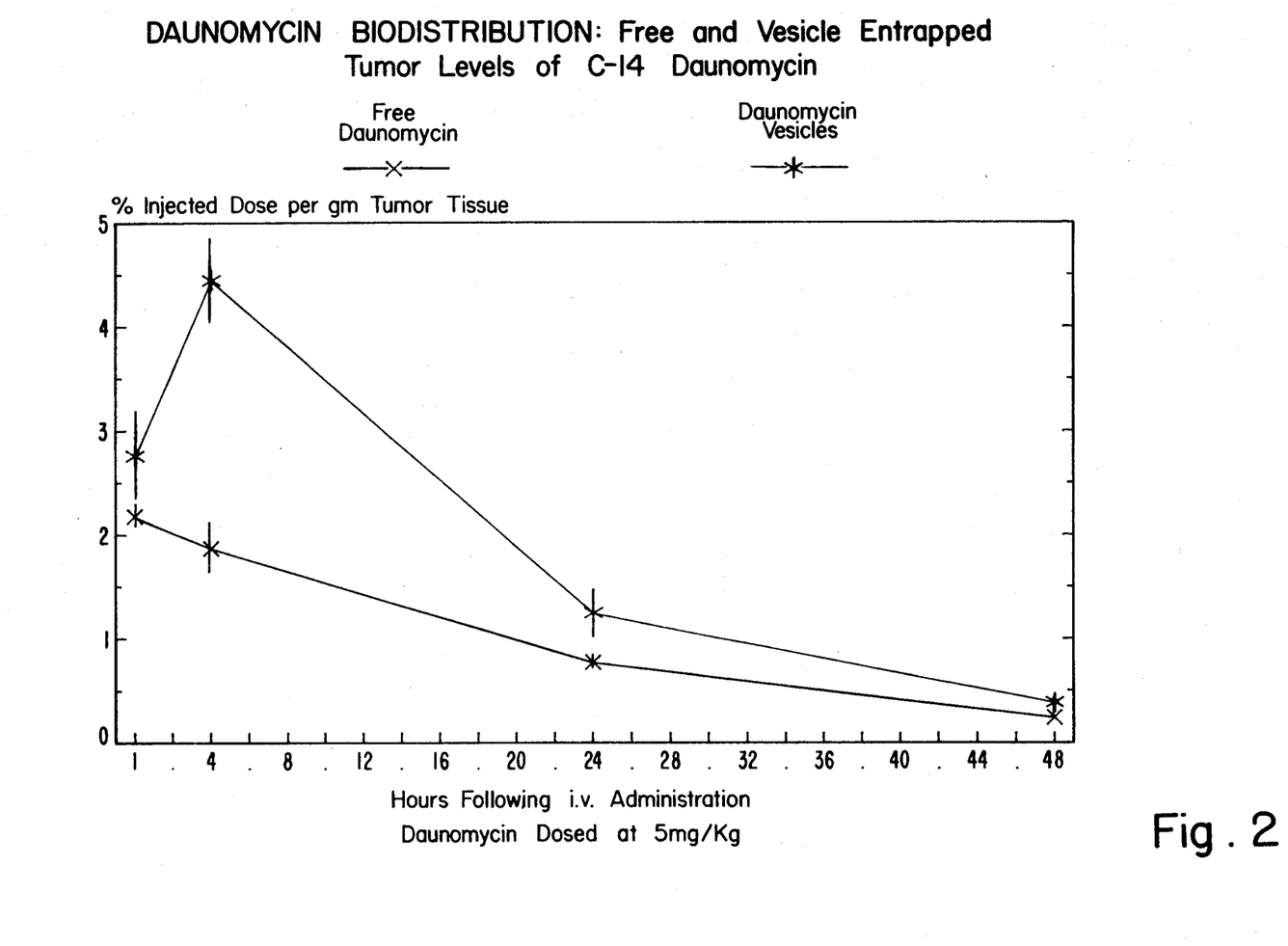
FIG. 2 illustrates the in vivo levels (biodistribution) of C-14 labeled daunorubicin, free and vesicle entrapped in solid tumors in mice at 1, 4, 24 and 48 hours.
Figure 3:
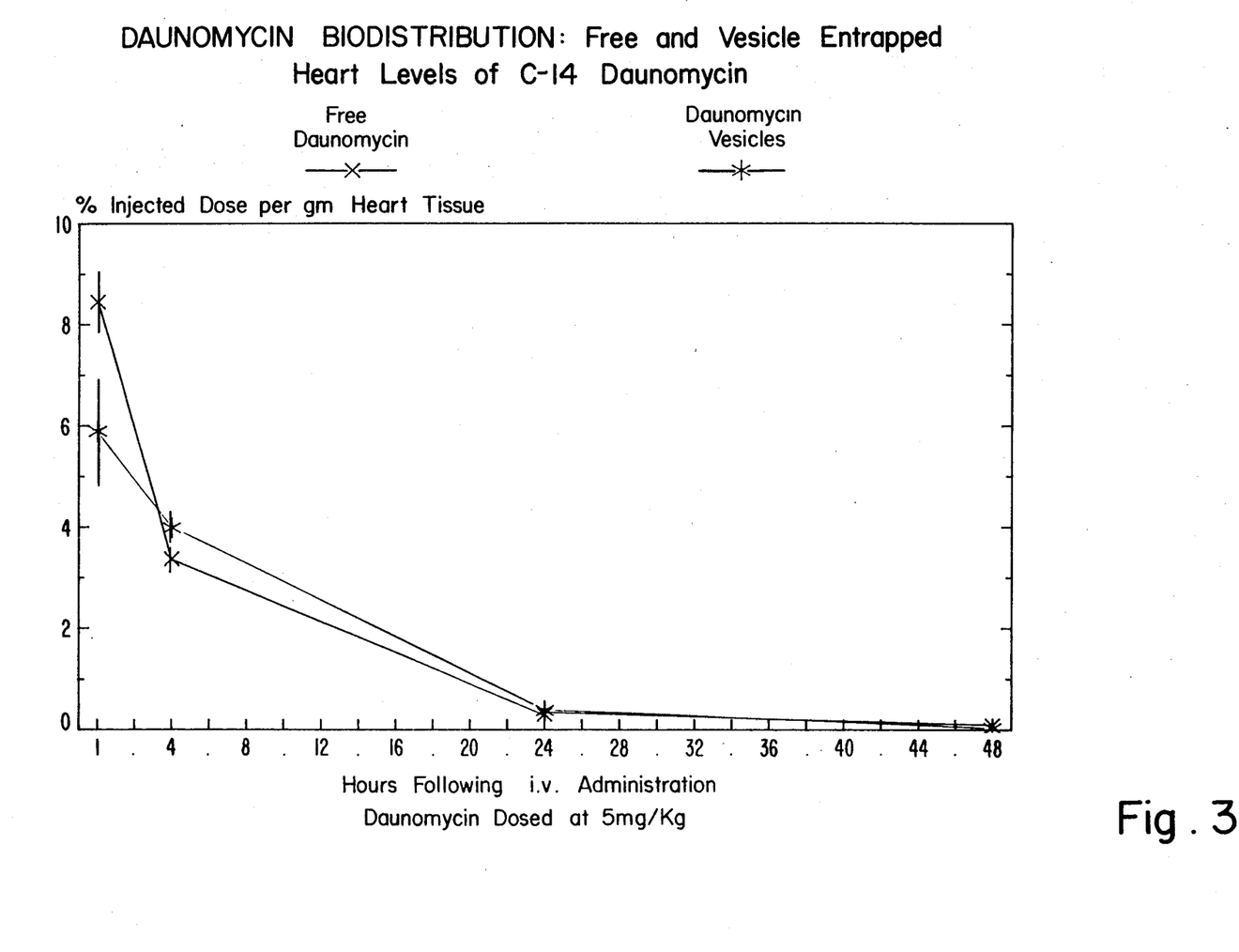
FIG. 3 illustrates the in vivo levels (biodistribution) of C-14 labeled daunorubicin, free and vesicle entrapped in heart tissue in mice at 1, 4, 24 and 48 hours.
Figure 4:
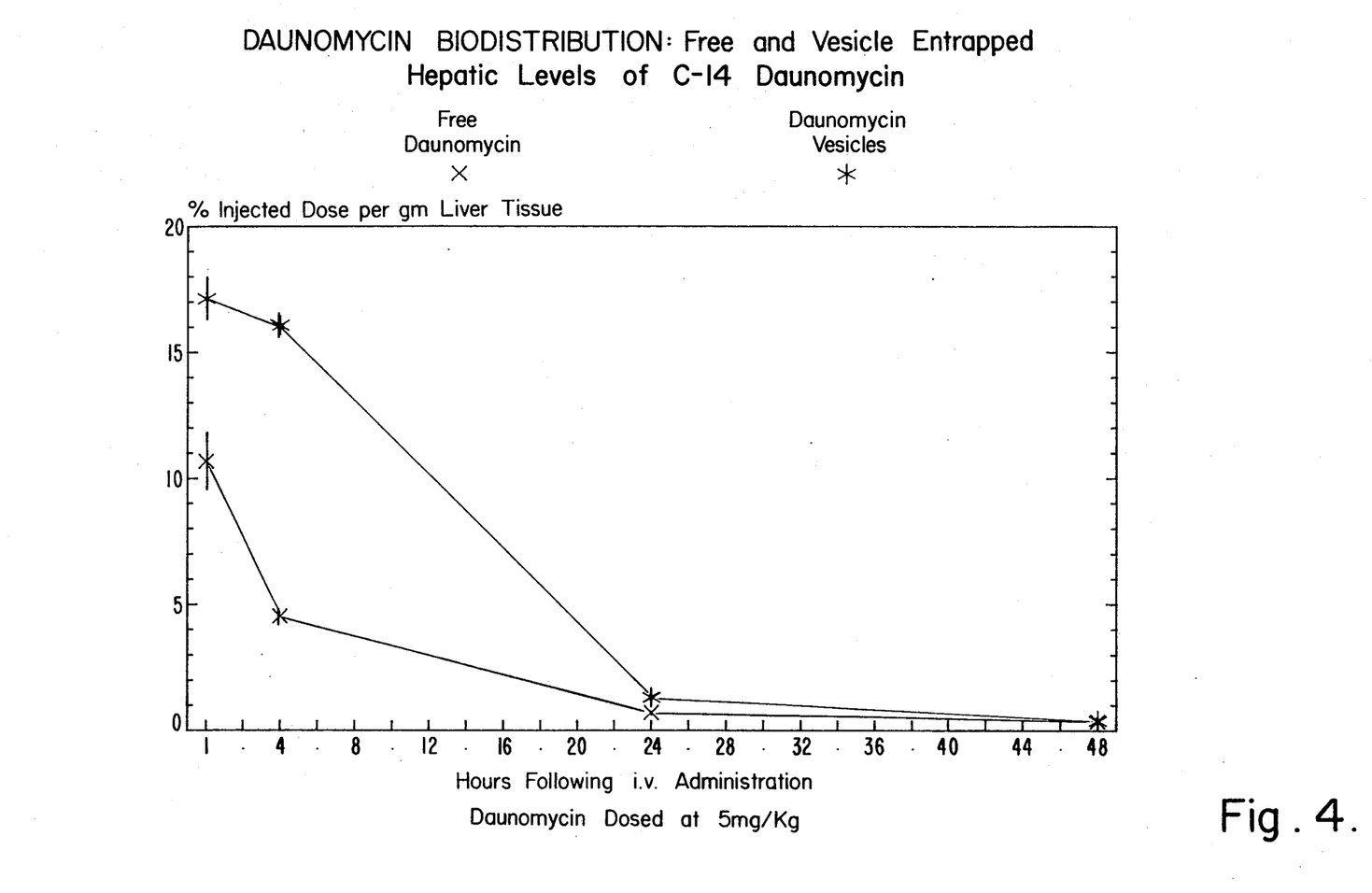
FIG. 4 illustrates the in vivo hepatic levels (biodistribution) of C-14 labeled daunorubicin, free and vesicle entrapped in mice at 1, 4, 24 and 48 hours.
Figure 5:
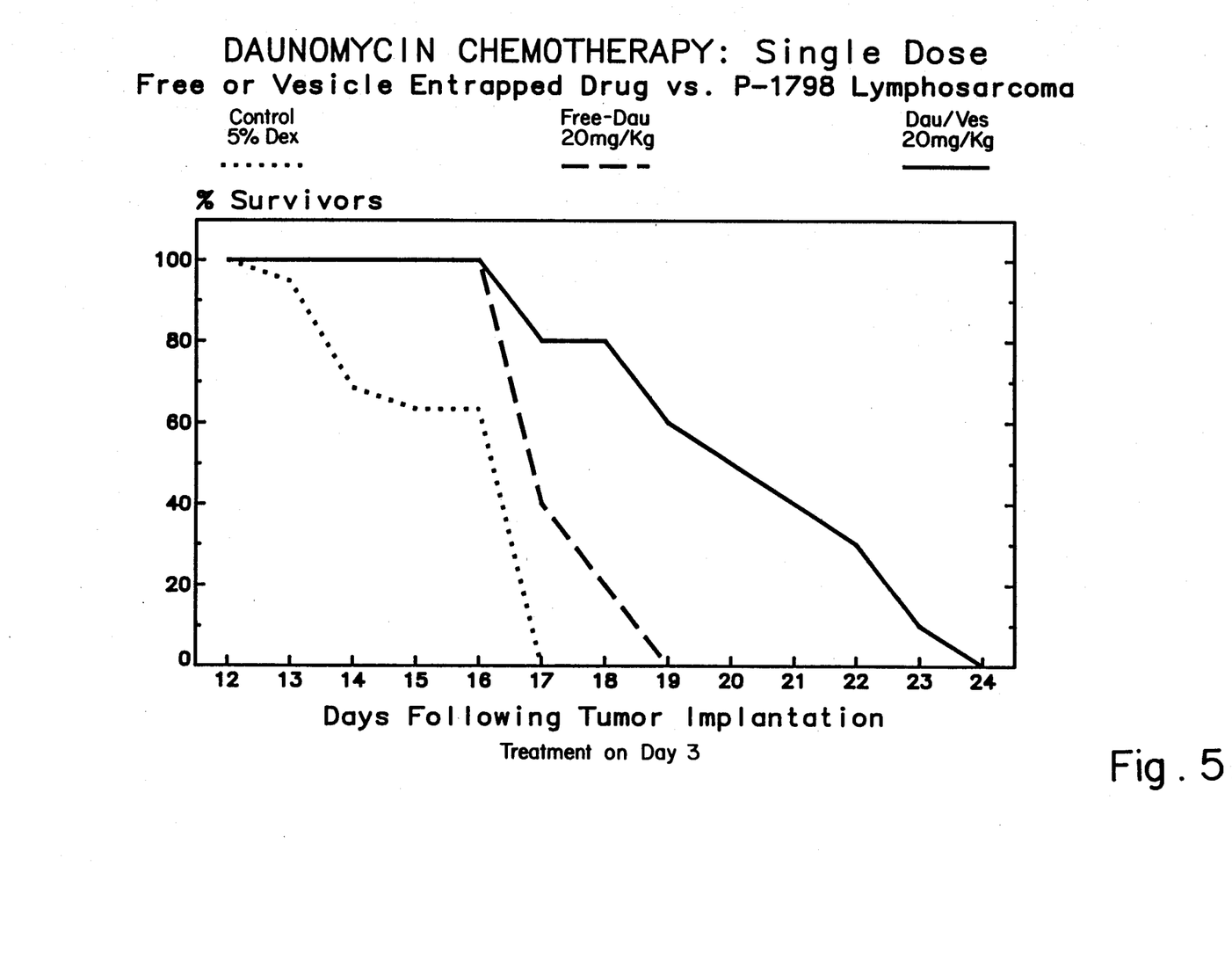
FIG. 5 depicts the rate of survival in mice bearing solid tumors treated on day 3 with a single dose of free or vesicle-entrapped daunorubicin.
Figure 6:
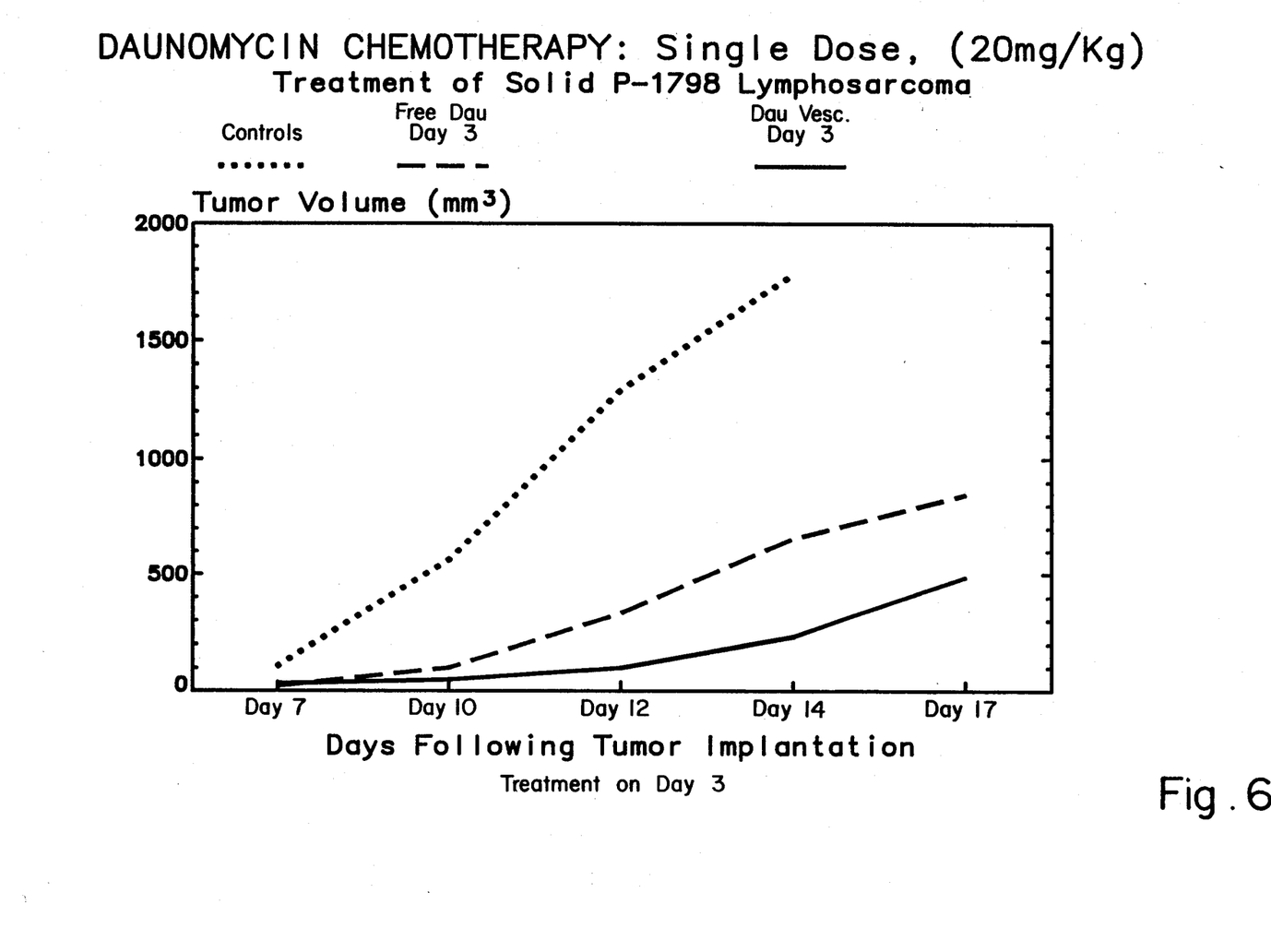
FIG. 6 shows the effect on tumor volume of single doses of daunorubicin, free or vesicle-entrapped, administered to mice bearing solid tumors.

Representative results of these investigations are shown in FIG. 5 for treatment commencing on day 3 after tumor implantation. Typically, with tumor metastasis, mice with tumors die within 14–17 days. Survival times for daunorubicin-vesicle treated mice increased in comparison to free drug. The median life span of mice injected with daunorubicin-vesicles was 21 days. All mice receiving free or vesicle entrapped daunorubicin demonstrated significant inhibition of tumor growth compared with untreated controls. Mice receiving vesicle entrapped daunorubicin had less tumor growth than those receiving free doses, as depicted in FIG. 6.

Figure 7:
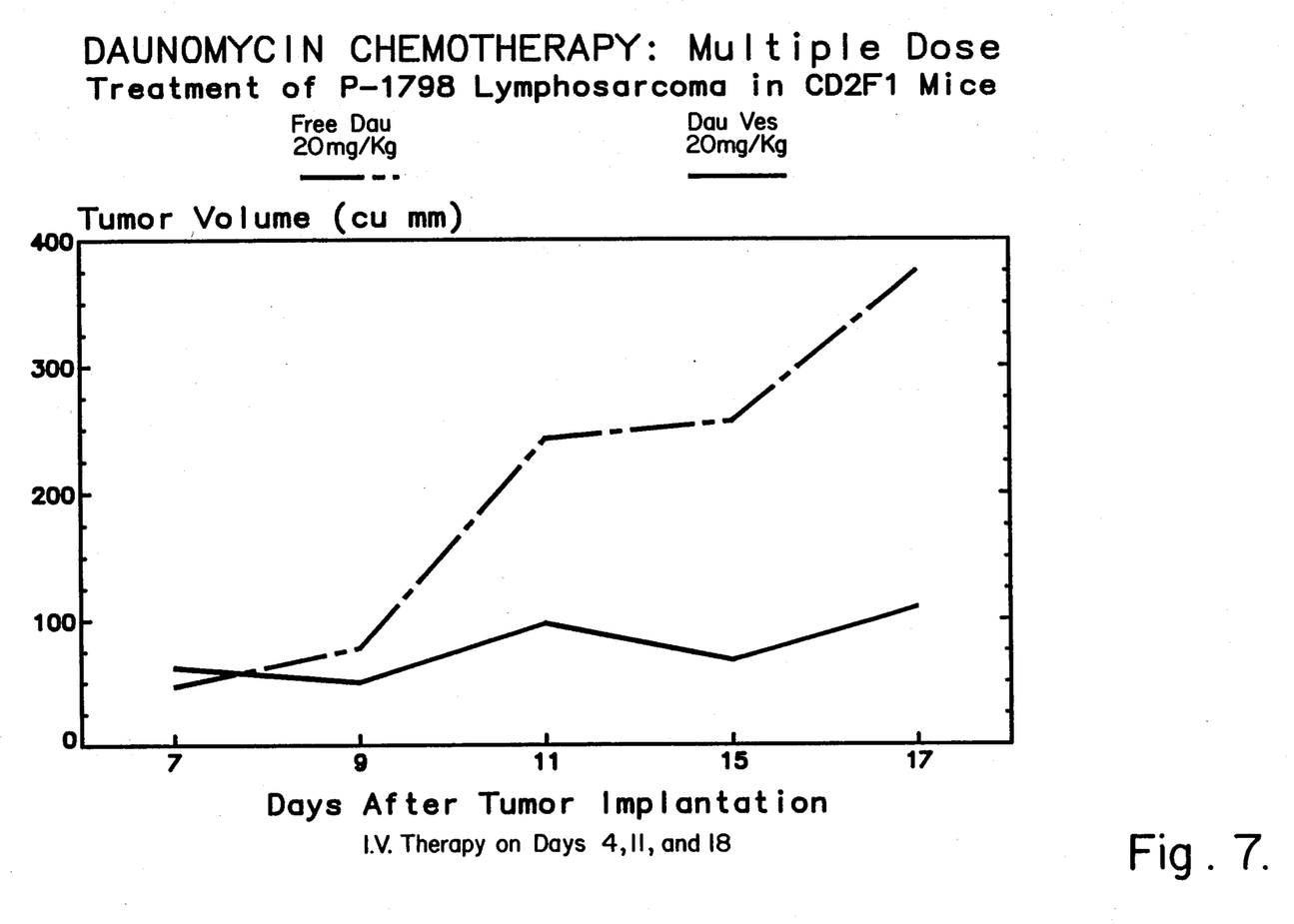
FIG. 7 illustrates the effect on tumor volume of multiple (20 mg/kg) doses of free or vesicle entrapped daunorubicin in mice bearing solid tumors.
Figure 8:
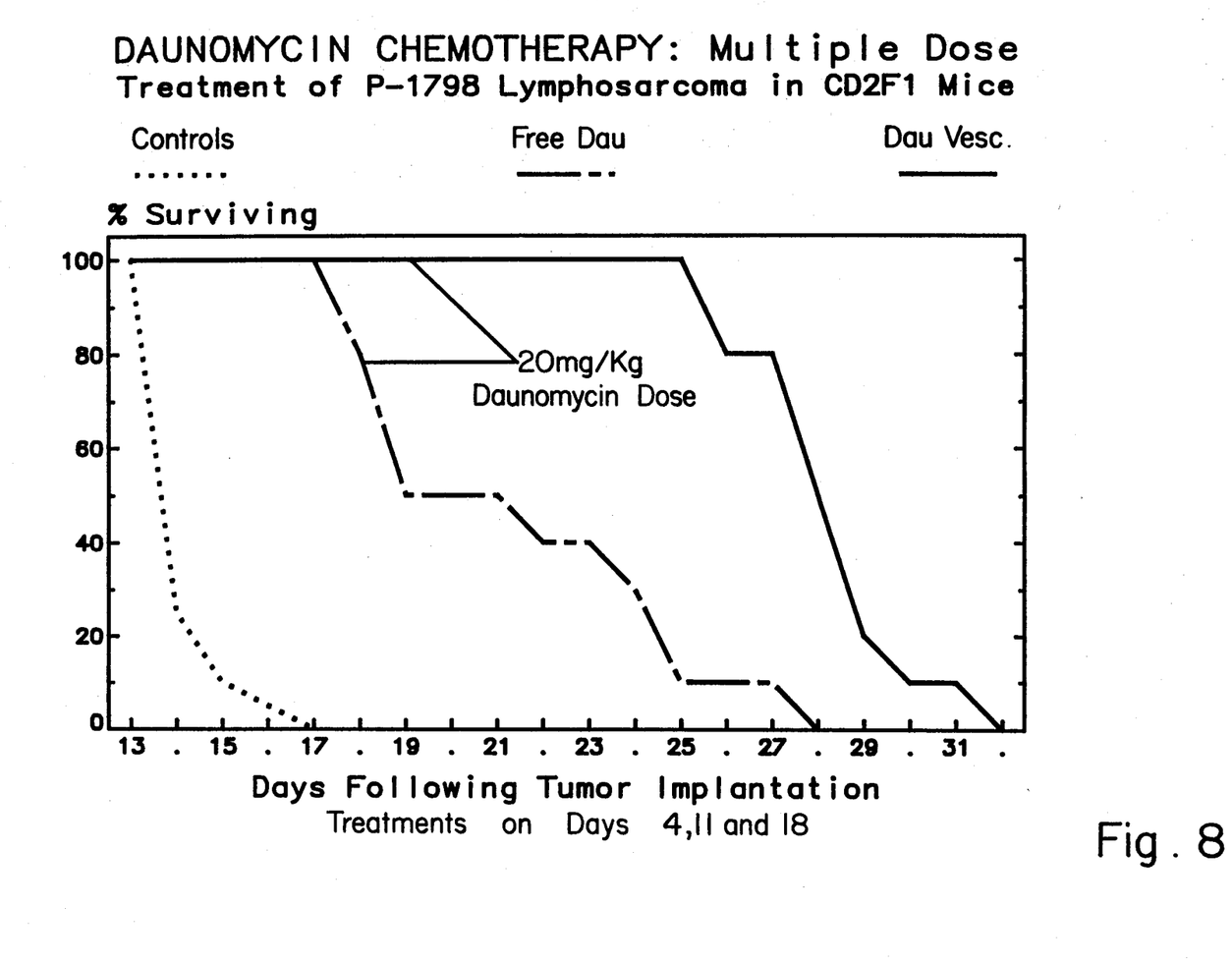
FIG. 8 depicts the survival rate for mice bearing solid tumors and receiving multiple doses (20 mg/kg) of free or vesicle entrapped daunorubicin.

In a second study of chemotherapeutic effects of injections of daunorubicin-vesicles, groups of ten mice received multiple doses of 5, 10 and mg/kg. Treatments were initiated on day 4 and followed at weekly intervals (day 11, day 18) for a total of three doses. Body weight and tumor size were monitored during the study. As shown in FIG. 7, at 20 mg/kg significant inhibition of tumor growth occurred in daunorubicin-vesicle treated mice compared with those treated with free drug. Survival times were investigated in a group of 19 mice and as indicated in FIG. 8 following tumor implantation were significantly increased for daunorubicin-vesicle treated mice relative to free drug at doses of 20 mg/kg.

These results clearly demonstrate the usefulness and efficacy of the vesicle formulations of the present invention as improved vehicles for delivering anthracyclines to tumors in a body.

EXAMPLES II–IV

The procedure of Example IA above was repeated in every essential detail except for the materials used to prepare the anthracycline anti-neoplastic agent-containing phospholipid vesicles, i.e.:

in Example II radioactive labeled (tritiated) daunorubicin was used to prepare vesicles having the same DAU:DSPG:DSPC:CHOL molar ratio (1:4:5:6, respectively) as in Example IA (cholesterol was used);

in Example III the vesicles were prepared using tritiated daunorubicin with distearoyl phosphatidylglycerol and distearoyl phosphatidylcholine in a molar ratio of DAU:DSPG:DSPC=1:1.5:7, respectively (no cholesterol was used);

in Example IV the vesicles were prepared in a DAU(-tritiated):DSPG:DSPC:CHOL molar ratio of 1:1.5:7:2, respectively (cholesterol was used);

a 9% lactose solution in deionized distilled water containing 5 mM TRIS base was used in each instance as the low ionic strength aqueous phase.

The uptake of tritiated daunorubicin by whole blood, tumor tissue (P-1798 lymphosarcoma) and thre other tissues in mice was then determined for the daunorubicin-containing vesicles of Examples II, III and IV, for free daunorubicin and for daunorubicin simply admixed with distearoyl phosphatidylglycerol in a 1:1 mol ratio. In all cases the administered dose of daunorubicin was 20 mg/kg (normalized to the hydrochloride form; equivalent to about 35.5 μM/kg). The results of these determinations are shown graphically in FIG. 9, in which the numbers below the legends "Dau:Ves." indicate the mol ratios of each component in the particular formulation [the first formulation listed under the legend "Dau:Ves." (1:1.5:7:0) is that of Example III, the second (1:1.5:7:2) is that of Example IV, the third is that of Example II].

Figure 9:
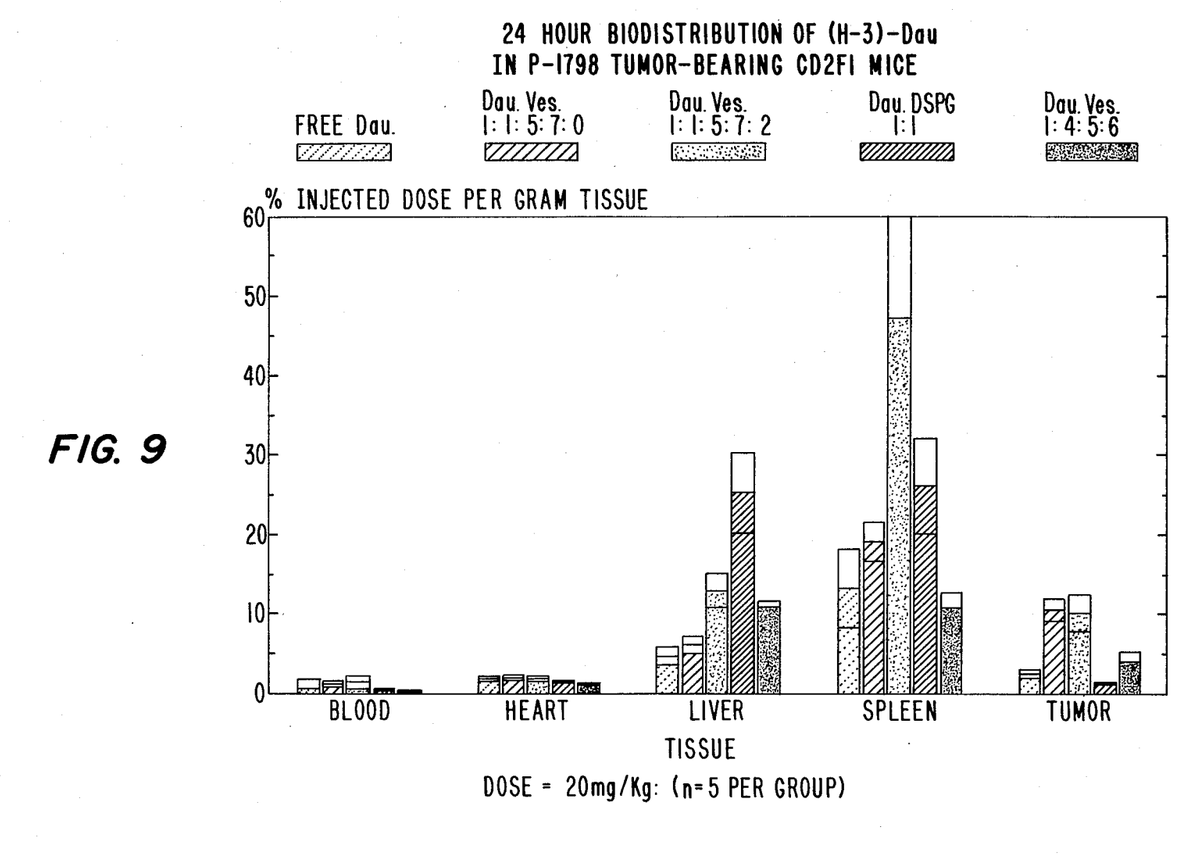

As indicated in FIG. 9, merely combining daunorubicin with distearoyl phosphatidylglycerol produced no increase in tumor uptake. A vesicle formulation with a relatively high proportion of distearoyl phosphatidylglycerol (1:4:5:6; Example II) did increase tumor drug levels over those for free daunorubicin. However, two other formulations, either with (1:1.5:7:2; Example IV) or without cholesterol (1:1.5:7:0), which had lower mol proportions of distearoyl phosphatidylcholine produced even greater tumor drug levels.

Figure 10:
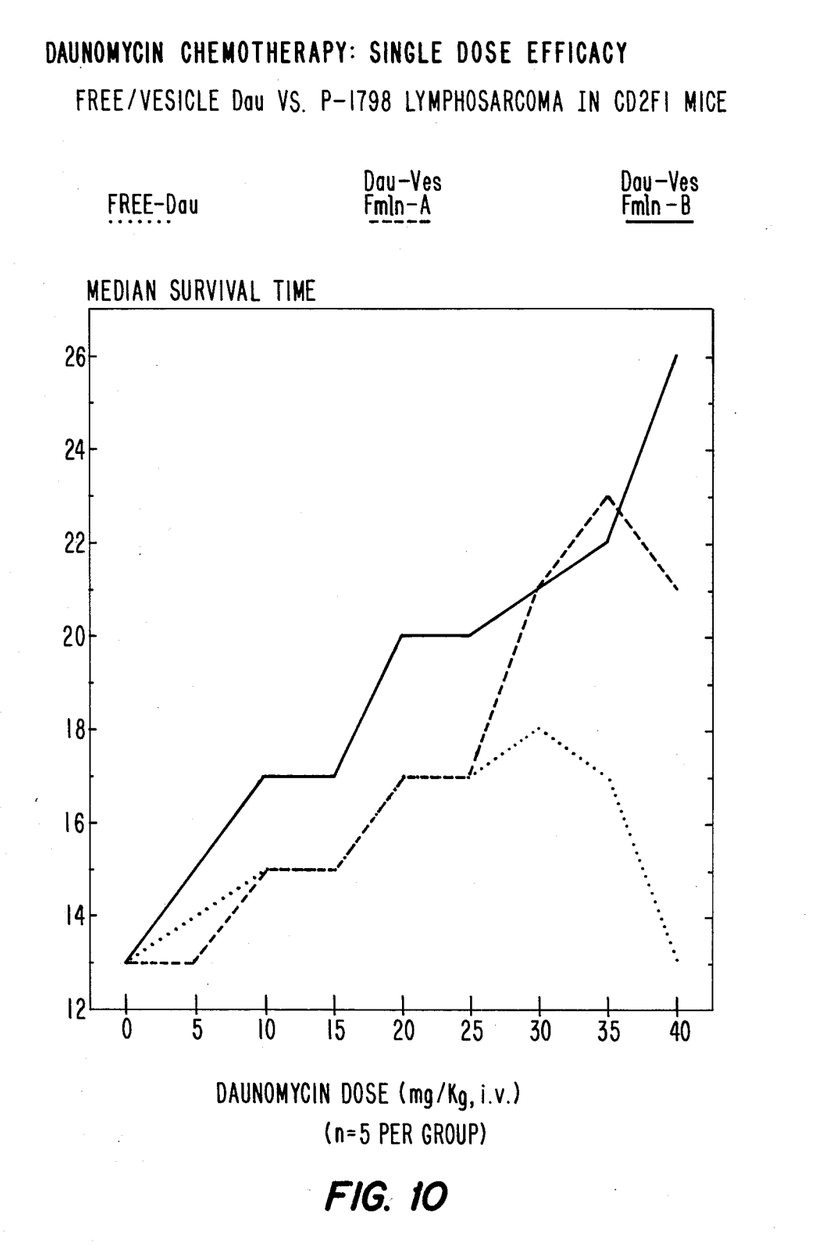
FIG. 10 indicates the therapeutic effects of the daunorubicin-containing vesicle formulations of Examples II and IV hereinbelow, compared to each other and to free daunorubicin, for a solid tumor in mice.

The therapeutic effects of the daunorubicin-containing vesicle formulations of Examples II and IV, indicated in FIG. 10 as "Fmln-A" and "Fmln-B", respectively, were compared to each other and to free daunorubicin for a solid tumor in mice. The results shown in FIG. 10 indicate that the formulation with the lower targeting ability (Fmln-A) did little to improve median survival times relative to free daunorubicin at doses of 25 mg/kg or below. Only when tested at dose levels of 30 mg/kg and above did Fmln-A demonstrate improved efficacy. However, the formulation with improved targeting characteristics (Fmln-B) demonstrated improved therapeutic efficacy at all tested dose levels.

Figure 11:
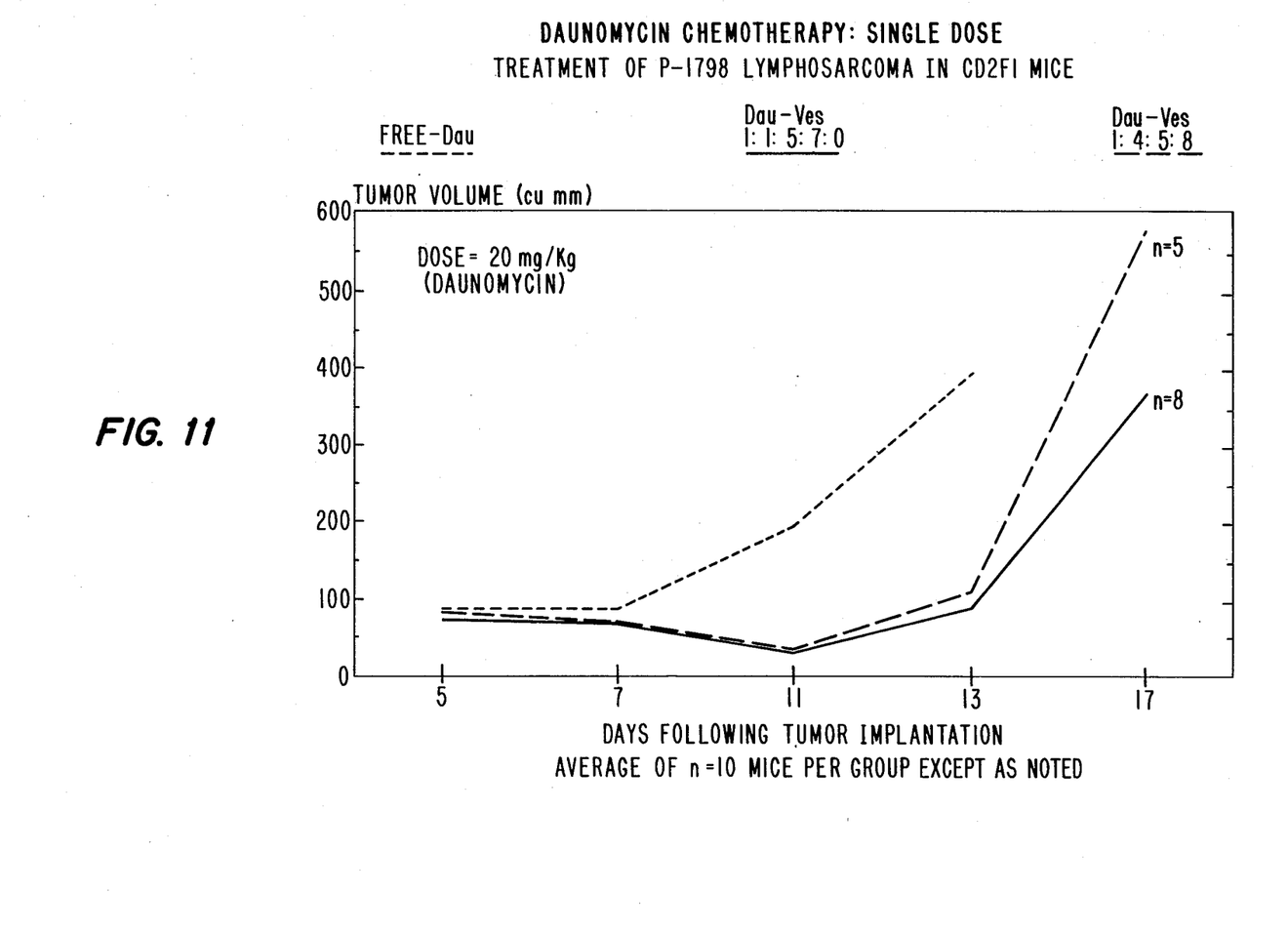
FIG. 11 illustrates the results of a study on the effect on tumor sizes of the daunorubicin-containing vesicle formulations of Examples II and IV hereinbelow.

Tumor sizes were determined in a repeated study of Fmln-A and Fmln-B. The results of this study, shown in FIG. 11, demonstrated that the formulation which does target more effectively to tumor tissue (Fmln-B) has the direct effect of enhancing tumor growth suppression.

EXAMPLE V

Figure 12:
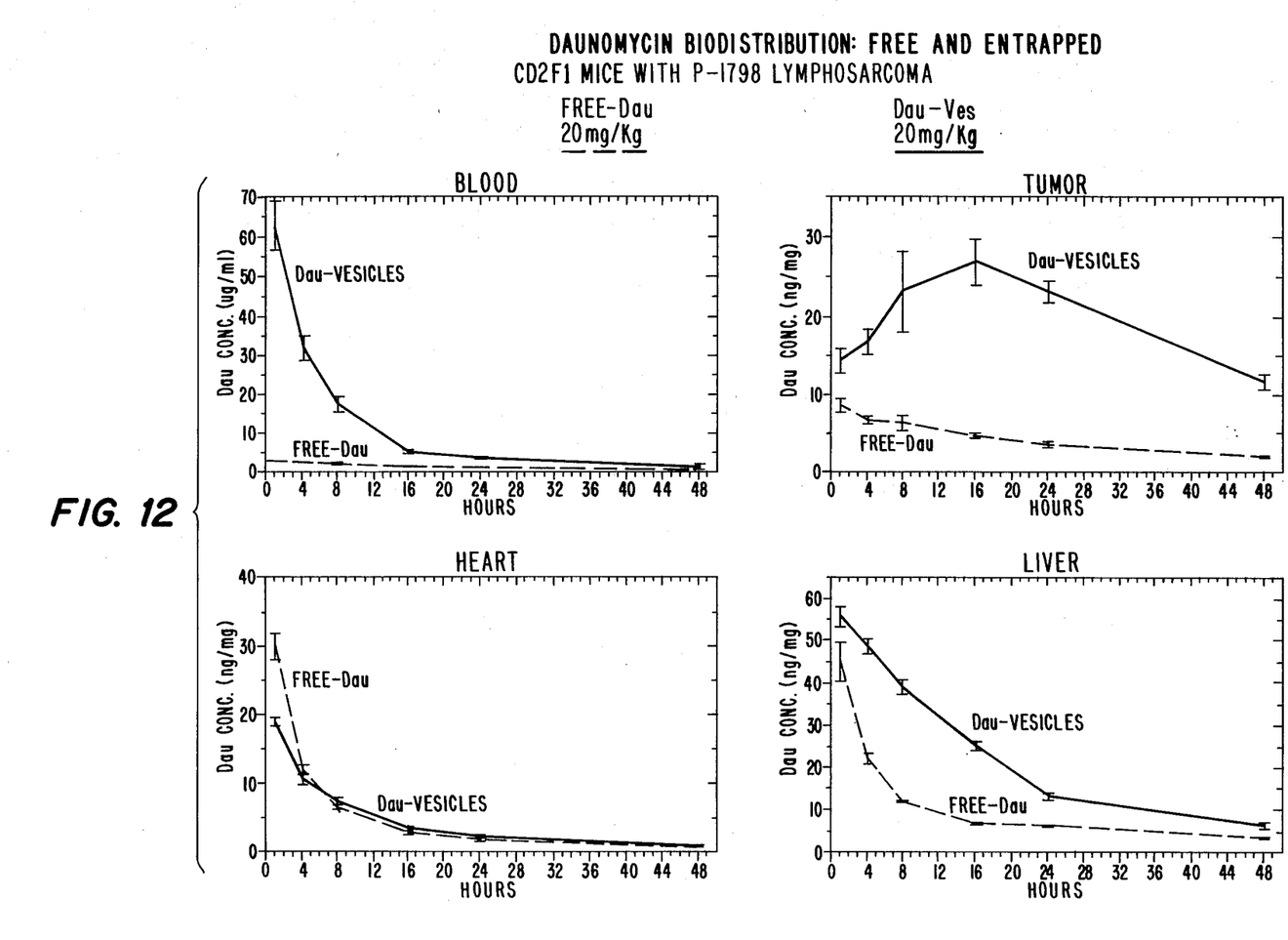
FIG. 12 illustrates the in vivo levels (biodistribution) of tritiated daunorubicin, free and vesicle entrapped (Example III hereinbelow), in the blood, in solid tumors, in heart tissue and in the livers of mice over a 48 hour period.

Biodistribution studies of tritiated daunorubicin, both free and vesicle entrapped (DAU:DSPG:DSPC mol ratio=1:1.5:7; Example III hereinabove) were conducted over a 48 hour period using a daunorubicin dose of 20 mg/kg in $CD_2F_1$ mice bearing intradermal P-1798 lymphosarcoma solid tumor. The results of these studies are illustrated in FIG. 12, in which the error bars are for the standard error, n=5 for each data point.

Although this invention has been described with reference to particular applications, the principles involved are susceptible of other applications which will be apparent to those skilled in the art. The invention is, therefore, to be limited only as indicated by the scope of the claims appended hereto.

I claim:

1. A composition comprising an anthracycline anti-neoplastic agent encapsulated in phospholipid bilayer membrane particles consisting of anionic and neutral phospholipids, said particles being suspended in a low ionic strength aqueous phase, the mol ratio of anthracycline anti-neoplastic agent to anionic phospholipid being at least about 1:1.25.

2. A composition according to claim 1 wherein the low ionic strength aqueous phase contains a physiologically acceptable nonionic hydroxyl-containing compound.

3. A composition according to claim 2 wherein the hydroxyl-containing compound is a sugar.

4. A composition according to claim 3 wherein the sugar is a monosaccharide.

5. A composition according to claim 4 wherein the monosaccharide is dextrose.

6. A composition according to claim 3 wherein the sugar is a disaccharide.

7. A composition according to claim 6 wherein the disaccharide is lactose.

8. A composition according to claim 7 wherein the lactose is present as a 9-11% solution and the pH is about 6.0 to 8.0.

9. A composition according to claim 1 wherein the anionic phospholipid is a phosphatidylglycerol, phosphatidylserine, phosphatidylinositol or phosphatidic acid and the neutral phospholipid is a phosphatidyl choline or phosphatidylethanolamine.

10. A composition according to claim 9 wherein cholesterol is also present.

11. A composition according to claim 9 wherein the anionic phospholipid is distearoyl phosphatidylglycerol and the neutral phospholipid is distearoyl phosphatidylcholine.

12. A composition according to claim 11 wherein the anthracycline anti-neoplastic agent, distearoyl phosphatidylglycerol and distearoyl phosphatidyl choline are in the molar ratio of 1:1.5:7

13. A composition according to claim 10 wherein the anthracycline anti-neoplastic agent, distearoyl phosphatidylglycerol, distearoyl phosphatidyl choline and cholesterol ar in the molar ratio of 1:1.5:7:2.

14. A composition according to claim 10 wherein the anthracycline anti-neoplastic agent, distearoyl phosphatidylglycerol, distearoyl phosphatidylcholine and cholesterol are in the molar ratio of 1:4:5:6.

15. A composition according to any one of claims 1-14, inclusive, wherein the antracycline anti-neoplastic agent is selected from the group consisting of daunorubicin, doxorubicin and Aclacinomycin A.

16. A composition according to claim 15 wherein the anthracycline anti-neoplastic agent is daunorubicin.

17. A method for treating neoplastic tumors in a human body affected therewith comprising parenterally administering to said human body multiple doses of a composition of claim 15.

18. A method according to claim 17 wherein administration is by intraveneous injection.

* * * * *